United States Patent [19]
Janulis

[11] Patent Number: 5,205,158
[45] Date of Patent: Apr. 27, 1993

[54] SAMPLING RHEOMETER AND METHOD
[75] Inventor: Theodore N. Janulis, West Orange, N.J.
[73] Assignee: Rheometrics, Inc., Piscataway, N.J.
[21] Appl. No.: 736,576
[22] Filed: Jul. 26, 1991
[51] Int. Cl.$^5$ .......................... G01N 11/04
[52] U.S. Cl. ................. 73/54.06
[58] Field of Search ......... 73/55, 56, 863.51, 863.52, 73/863.57, 863.71, 864.81, 54.04–54.06

[56] References Cited

U.S. PATENT DOCUMENTS

| | | | |
|---|---|---|---|
| 1,190,085 | 7/1916 | Bauer | 73/56 |
| 2,736,201 | 2/1956 | Ohlsen et al. | 73/863.57 |
| 3,138,950 | 6/1964 | Welty et al. | 73/56 |
| 3,167,950 | 2/1965 | Gamlen | 73/56 |
| 3,638,476 | 2/1972 | Paterson et al. | 73/863.51 |
| 3,758,776 | 9/1973 | Frohne et al. | 73/56 |
| 4,346,609 | 8/1982 | Diesel | 73/863.51 |
| 4,539,837 | 9/1985 | Barnaby | 73/55 |
| 4,680,958 | 7/1987 | Ruelle et al. | 73/56 |

FOREIGN PATENT DOCUMENTS 1111373 4/1968 United Kingdom ............. 73/56

Primary Examiner—Robert Raevis
Attorney, Agent, or Firm—Samuelson & Jacob

[57] ABSTRACT

A rheometer and a method for measuring rheological properties of a fluid material, especially in an in-line arrangement in a manufacturing process, include capturing and confining a volume of the fluid material against movement within a chamber, advancing an orifice plate having an orifice into the confined volume of the fluid material in the chamber such that the fluid material flows relative to the orifice to pass through the orifice plate, and determining the pressure in the confined volume of fluid material as the orifice plate is advanced into the chamber and through the confined volume of fluid material and the fluid material passes through the orifice, the pressure being indicative of the rheological properties being measured.

7 Claims, 4 Drawing Sheets

FIG. 7.
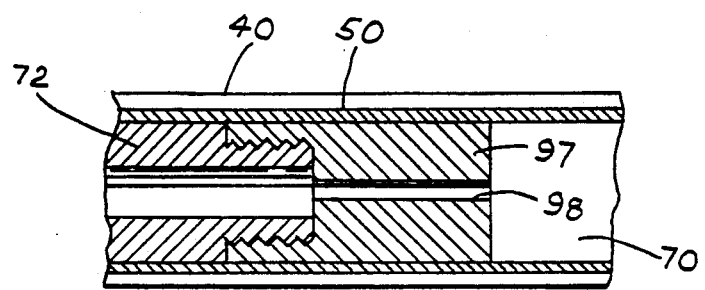
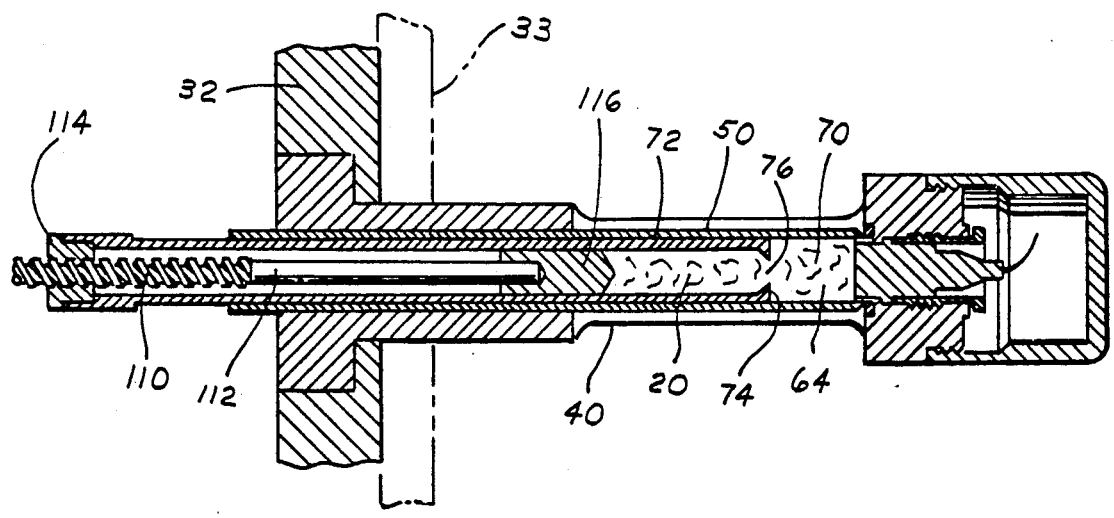
FIG. 8.

SAMPLING RHEOMETER AND METHOD

The present invention relates generally to the measurement of physical characteristics of materials and pertains, more specifically, to rheometers and to methods for measuring rheological properties of fluid materials.

The current emphasis on maintaining high quality in high volume production processes involving fluid materials, as in the manufacture of baked goods such as cookies and crackers, where the end product is produced by baking a carefully prepared dough, has led to the requirement for measuring instruments and techniques which can furnish accurate information pertaining to the condition of the fluid material as the material is utilized in the process, or "in-line". Such instruments and methods must operate rapidly and with great accuracy to provide data which enables control of the process within the close tolerances required for consistent high quality, without interfering with the process itself and without excessive waste.

The present invention provides a rheometer and method for the rapid and accurate measurement of viscosity in samples of fluid materials being processed into finished products, and which are especially well-suited to in-line operation where samples must be tested quickly and accurately for close control of the process being monitored. One such process is the manufacture of baked goods, such as cookies and crackers, wherein a carefully prepared dough is baked to produce the finished product. The quality of the end product is determined to a great extent by the consistency of the dough and it would be advantageous to have available apparatus and method for measuring rheological properties of the dough regularly during the process, as the dough is completed and before the dough is cut into a desired shape and then baked. For such purposes, an important rheological property is viscosity and, more particularly, extensional viscosity. The present invention enables the measurement of viscosity in fluid materials, such as cookie and cracker dough, on an in-line basis, for accurate control of the process by which these products are produced and exhibits several objects and advantages, some of which may be summarized as follows: provides for rapid sampling and accurate measurement of rheological properties of samples of fluid materials, for close control of the quality of the product of the process; enables the measurement of the viscosity of fluid materials, such as cookie and cracker doughs, with increased speed and accuracy, and is well-suited to in-line use; rapidly samples fluid materials in-line without disruption of the process involved and without excessive waste; attains accurate results in a wide range of materials over a variety of conditions; enables better control over processes which utilize fluid materials for consistent, high quality in the end products of such processes.

The above objects and advantages, as well as further objects and advantages, are attained by the present invention which may be described briefly as apparatus and method for measuring rheological properties of a fluid material, including means for and the step of confining a volume of the fluid material essentially against movement relative to the confining means; means for and the step of advancing orifice means into the confined volume of fluid material, the orifice means including an orifice through which the fluid material flows relative to the orifice means as the orifice means is advanced through the confined volume of fluid material; and means for and the step of determining the pressure in the confined volume of fluid material as the orifice means is advanced through the confined volume of fluid material, the determined pressure being indicative of the rheological properties to be measured.

The invention will be understood more fully, while still further objects and advantages will become apparent, in the following detailed description of preferred embodiments of the invention illustrated in the accompanying drawing, in which:

FIG. 7 is a fragmentary view similar to FIG. 6, but illustrating an alternate embodiment; and FIG. 8 is a longitudinal cross-sectional view similar to FIG. 6, but reduced in scale and illustrating an alternate construction.

Figure 1:
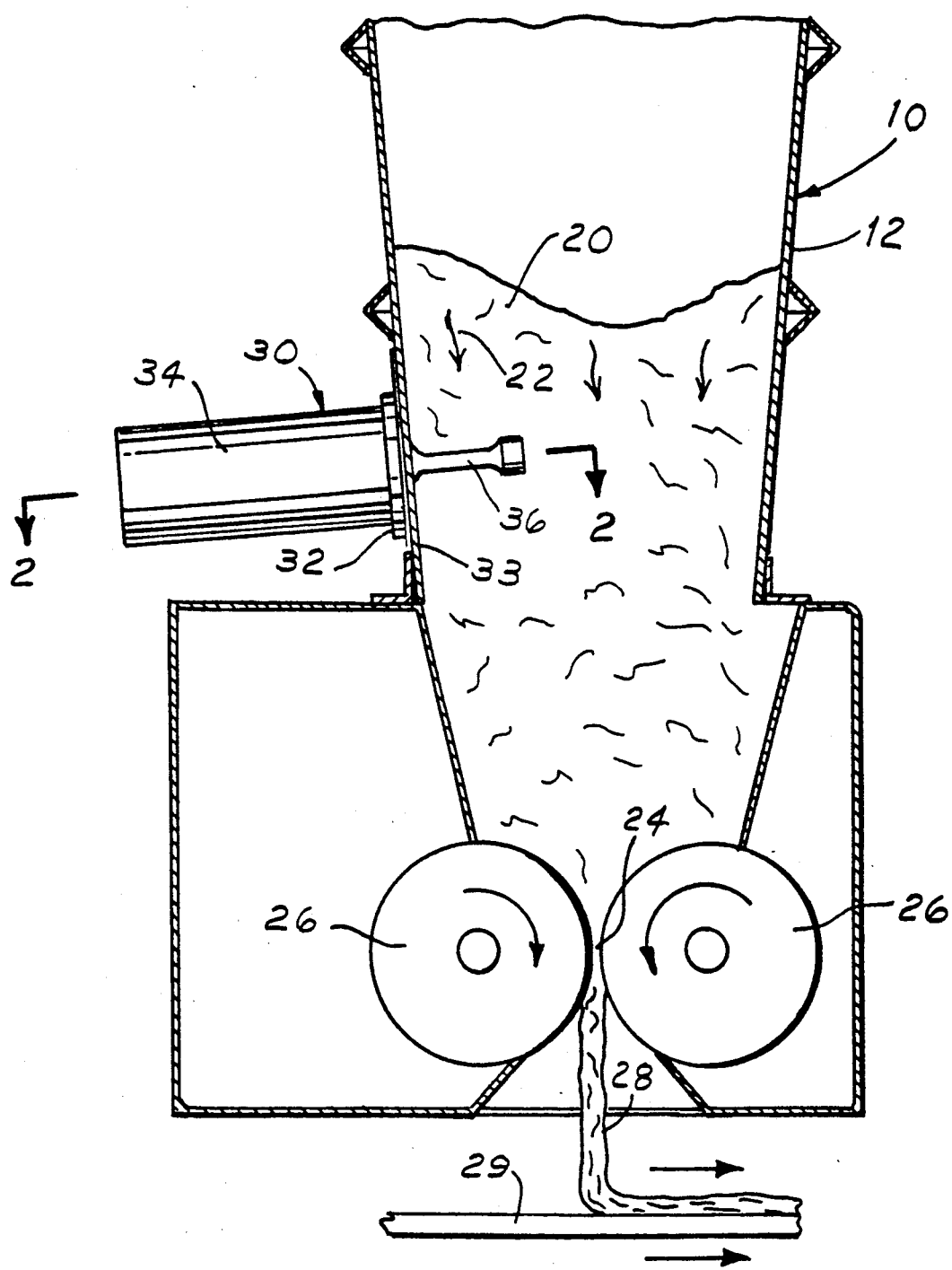
FIG. 1 is a somewhat diagrammatic cross-sectional view illustrating an in-line installation utilizing apparatus and method of the present invention.
Figure 2:
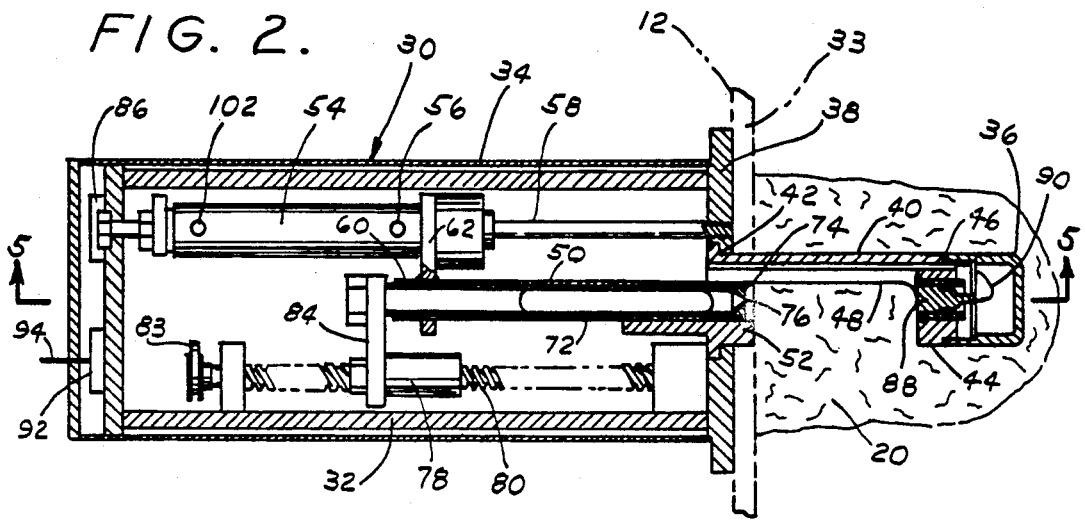
FIG. 2 is an enlarged, partially diagrammatic cross-sectional plan view taken along line 2—2 of FIG. 1.
Figure 3:
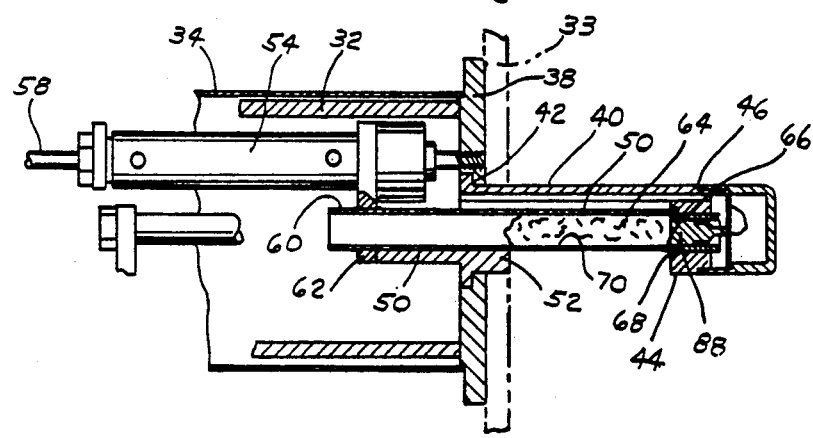
FIG. 3 is a fragmentary view of a portion of the apparatus of FIG. 2 illustrating component parts of the apparatus in a different operating position.

Referring now to the drawing, and especially to FIG. 1 thereof, a portion of processing apparatus for the manufacture of baked goods in the form of crackers is illustrated generally at 10 and is seen to include a hopper 12 into which is fed a carefully prepared cracker dough 20 having a controlled fluid consistency. Dough 20 proceeds downwardly in a stream 22 and passes through the nip 24 of a pair of rollers 26 to form the dough 20 into a sheet 28 which is then advanced, by a conveyor 29, to a machining stand (not shown) for cutting the sheeted dough into desired shapes prior to baking into finished crackers, all in a manner now well known in the preparation of baked goods. In order to control the consistency of the dough 20, and hence the quality of the end product, the dough 20 is sampled and the viscosity of the dough sample is measured to provide in-line testing of the dough 20 for effective process control. To that end, a rheometer 30, constructed in accordance with the present invention, is associated with the hopper 12, and is in communication with the stream 22 of dough 20, to measure the viscosity of the dough 20 in accordance with the method of the present invention. Rheometer 30 is seen to have a frame 32 mounted directly on the wall 33 of the hopper 12 and carrying a housing 34 outside the hopper 12. The frame 32 includes a probe 36 projecting into the hopper 12 to extend into the dough 20, transversely across the path of flow of the stream 22 of dough 20 as the dough 20 flows downwardly through the conduit established by the hopper 12.

Turning now to FIGS. 2 through 6, as well as to FIG. 1, frame 32 includes a flange 38 affixed to the wall 33 of the hopper 12 and the probe 36 of the frame 32 includes a bridge 40 passing through the wall 33 to extend from the wall 33, at the near end 42 of the bridge 40, into the stream 22 of dough 20 flowing through the hopper 12. A support ring 44 is integral with the bridge 40 at the far end 46 of the bridge 40, and is spaced away from the near end 42 and the wall 33 of the hopper 12. The arrangement provides an opening 48 extending along the probe 36, between the near end 42 and the far end 46 of the bridge 40, the opening 48 passing through the probe 36 in the direction of flow of the stream 22 of dough 20 to enable dough 20 to pass through the opening 48, and the probe 36. When it is desired to measure the viscosity of the dough 20 in the hopper 12, the rheometer 30 is operated through a cycle of operation as follows: A tubular member in the form of a sleeve 50 mounted for axial sliding movement within a bushing 52 secured in flange 38 is advanced into the hopper 12 by virtue of the actuation of an actuator in the form of an air cylinder 54 in the housing 34. Air cylinder 54 moves in response to air under pressure supplied thereto at 56 to move air cylinder 54 along a piston rod 58, which is affixed to the frame 32, from the retracted position of the air cylinder 54 illustrated in FIG. 2 to the advanced position of the air cylinder 54 illustrated in FIGS. 3 and 4. Air cylinder 54 is coupled with sleeve 50 adjacent the near end 60 of the sleeve 50 by a connecting arm 62 so that as the air cylinder 54 is advanced, the sleeve 50 likewise is advanced and enters the stream 22 of dough 20 in the hopper 12 to span the opening 48 and collect a volume of dough 20 in the form of a sample 64 within the sleeve 50. Continued advancement of the sleeve 50 brings the far end 66 of the sleeve 50 to the support ring 44 wherein the far end 66 of the sleeve 50 engages a seal 68 placed in the support ring 44 to close the far end 66 of the sleeve 50, and the opening 48, and establish a closed chamber 70 within which the collected sample 64 of dough 20 is confined.

Figure 4:
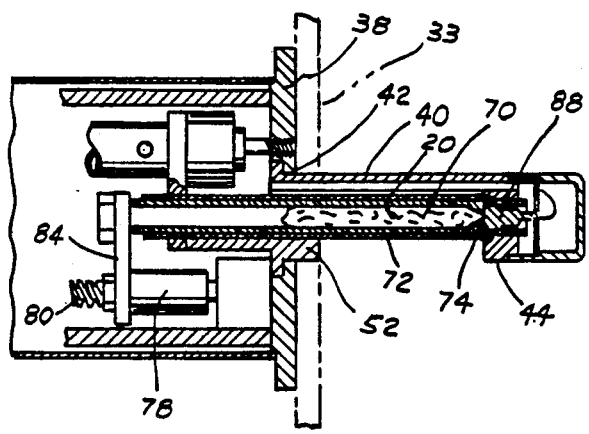
FIG. 4 is a fragmentary view of a portion of the apparatus of FIG. 2 illustrating the component parts of the apparatus in another operating position.

Once the sample 64 of dough 20 is captured in the chamber 70 by the capturing means described above, orifice means in the form of a cylindrical member illustrated as a piston 72 complementary with the sleeve 50 and having an end wall in the form of an orifice plate 74 with an orifice 76 therein is advanced into the chamber 70, as illustrated in FIG. 4, forcing the dough 20 of the captured sample 64 to pass through the orifice 76 as the piston 72 is urged toward the support ring 44. Advancement of the piston 72 and the orifice plate 74 carried thereby is accomplished by the movement of a follower 78 along a lead screw 80 journaled for rotation on the frame 32 and rotated by a motor 82, through a drive belt 83, the follower 78 being coupled to the piston 72 by a lateral piston arm 84. The motor 82 is controlled by a circuit 86 to impart a known rate of advancement to the piston 72 and the orifice plate 74 thereof. As the orifice plate 74 is advanced into the chamber 70, the pressure in the chamber 70, which pressure is a function of the known dimensions of the orifice 76, is detected by a transducer 88 mounted in the support ring 44 at the far end 46 of the bridge 40 and information pertaining to that pressure is transmitted, through an electrical conductor 90, to a further circuit 92 which processes the information and furnishes an output, at 94, indicative of the viscosity of sample 64 of dough 20 in the chamber 70.

By maintaining the transducer 88 stationary, relative to the chamber 70, while advancing the orifice plate 74 to establish the pressure measured by the transducer 88, the transducer 88 is subjected only to forces related to the pressure developed as a direct result of the fluid flow of the dough 20 of sample 64 through the orifice 76. Any frictional effects arising out of advancement of the piston 72 into the chamber 70, other than the pressure induced by the flow of material through the orifice 76, do not affect the pressure detected by the transducer 88. Further, the elimination of frictional effects by movement of the orifice plate 74 through the sample 64, as opposed to the more conventional arrangement wherein a sample fluid is forced through an orifice, enables more rapid stabilization and concomitant quicker response for reducing the time needed to obtain the desired pressure information. It is noted that unlike that more conventional arrangement, the present arrangement essentially eliminates all movement of the sample 64 except for displacement of the dough 20 of sample 64 through the orifice 76, thereby eliminating extraneous pressure effects and facilitating the measurement of only that pressure which is a result of the flow of material through- the orifice 76. Accordingly, the described arrangement attains increased accuracy effectively and with increased speed of operation.

Figure 6:
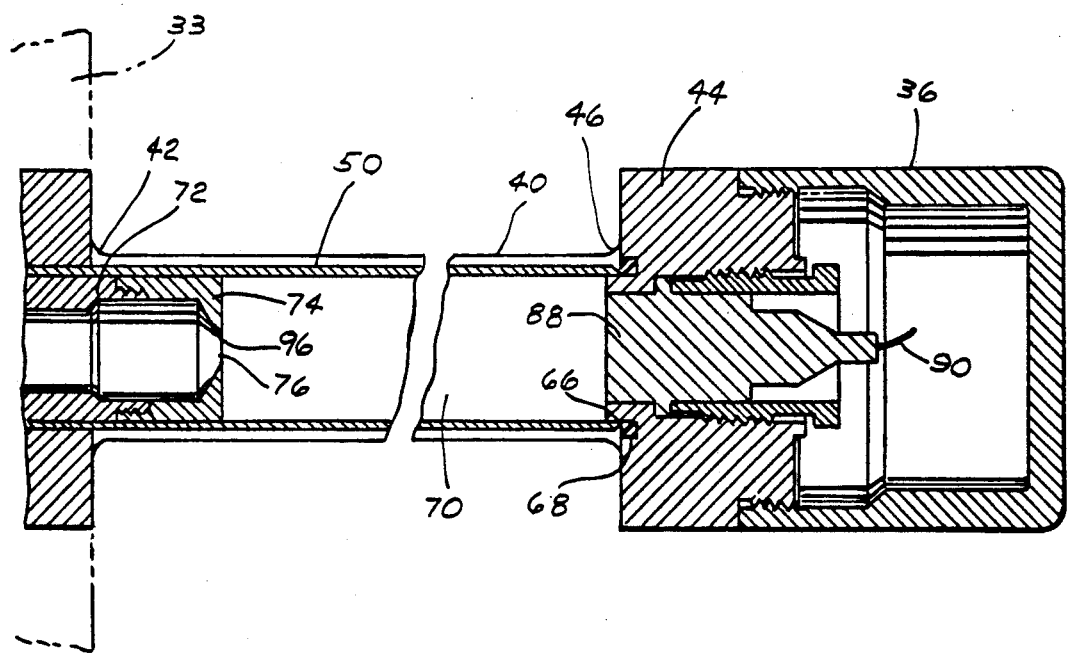
FIG. 6 is an enlarged fragmentary view of a portion of the apparatus of FIG. 5.

As best seen in FIG. 6, the orifice 76 is provided with a relatively sharp edge 96 along the periphery thereof so that the length of the orifice 76, in the axial direction of movement of the orifice plate 74 through the sample 64, is essentially zero. The zero-length orifice 76 provides for the measurement of elongational viscosity, the property which is most significant in evaluating the rheological qualities of fluid materials having a more paste-like consistency, such as dough 20. The quality of the measurement obtained is not affected by any sticking or any slipping of the material relative to the orifice plate 74, since the measurement is not a shear measurement. The information obtained is related only to pressure in the chamber 70. Since the sample 64 is confined within the chamber 70 and flow of the dough 20 of sample 64 is controlled so as to be only through the orifice 76, the pressure measurement is accomplished in an essentially closed system where the measurement can be fully controlled for exceptional accuracy as well as for increased speed of operation. Where it is desired to measure shear viscosity, rather than extensional viscosity, orifice plate 74 may be replaced by a capillary die, as seen at 97 in FIG. 7, in which the orifice is in the form of a capillary passage 98 of selected dimensions, in place of zero-length orifice 76.

Figure 5:
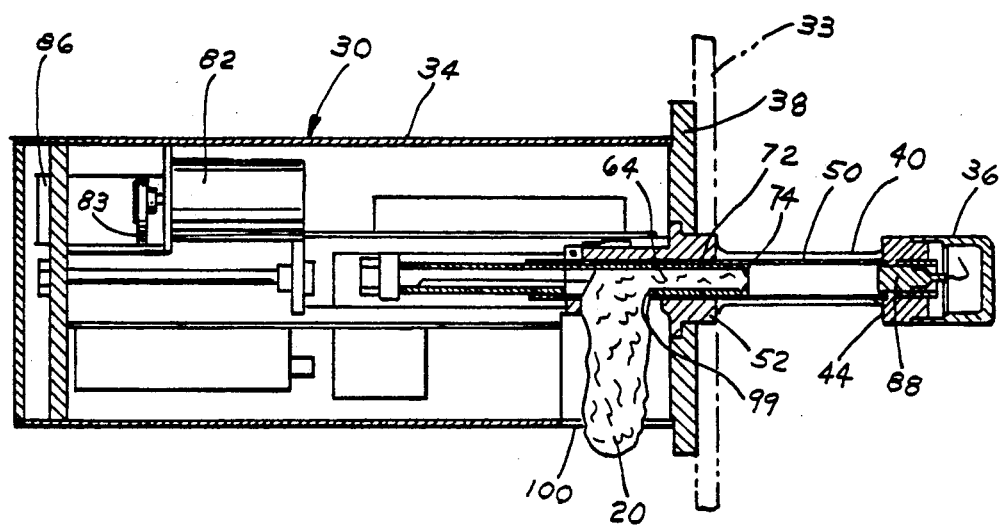
FIG. 5 is a cross-sectional elevational view taken along line 5—5 of FIG. 2, but with the component parts of the apparatus in still another operating position.

Upon completion of the advancement of the piston 72 into the sleeve 50, and obtaining of the desired data from the information provided by transducer 88, the piston 72 is retracted, by reversing the rotation of the lead screw 80, to withdraw the piston 72 from the chamber 70. Turning to FIG. 5, the dough 20 of the sample 64 which, as a result of passage through the orifice 76, now is behind the orifice plate 74, is retracted with the piston 72 and is directed through an exhaust port 99 for discard at 100. Once the piston 72 is retracted, the sleeve 50 is retracted by supplying air under pressure to the air cylinder 54, at 102, to effect retraction of the air cylinder 54 and concomitant retraction of the sleeve 50 to the retracted position shown in FIG. 2, and to ready the rheometer 30 for another cycle of operation.

In the alternate arrangement shown in FIG. 8, the piston 72 is advanced into the chamber 70 within sleeve 50 and is retracted from the chamber 70 by the rotation of a lead screw 110 carried by a drive shaft 112 mounted for rotation on the frame 32 and coupled to the piston 72 by a follower 114 affixed directly to the piston 72. During advancement of the piston 72 into the chamber 70, the sample 64 of dough 20 passes through orifice 76, as described in connection with the embodiment of FIGS. 2 through 6 above. However, upon retraction of the piston 72, a dynamic seal member 116 located on the drive shaft 112 remains stationary axially as the piston 72 is retracted, and the dough 20 which had passed through the orifice 76 and lies behind the orifice plate 74 is forced back through the orifice 76 to the chamber 70. Subsequent retraction of the sleeve 50 then enables return of the sample 64 of dough 20 to the stream 22 of dough 20 in the hopper 12, thereby reducing any waste which might have resulted from discard of the sample 64, as described in connection with the arrangement of FIG. 5.

It will be seen that the present invention provides both apparatus and method which attain the objects and advantages summarized above; namely, provides for rapid sampling and accurate measurement of rheological properties of samples of fluid materials, for close control of the quality of the product of the process; enables the measurement of the viscosity of fluid materials, such as cookie and cracker doughs, with increased speed and accuracy, and is well-suited to in-line use; rapidly samples fluid materials in-line without disruption of the process involved and without excessive waste; attains accurate results in a wide range of materials over a variety of conditions; enables better control over processes which utilized fluid materials for consistent, high quality in the end products of such processes.

It is to be understood that the above detailed description of preferred embodiments of the invention are provided by way of example only. Various details of design, construction and procedure may be modified without departing from the true spirit and scope of the invention as set forth in the appended claims.

The embodiments of the invention in which an exclusive property or privilege is claimed are defined as follows:

1. An in-line rheometer for measuring rheological properties of a fluid material flowing in a stream along a path of flow in a given direction through a conduit in a processing apparatus, the conduit having a conduit wall, the rheometer comprising:

a frame for projecting into the conduit from a near end at the conduit wall to a far end spaced from the conduit wall, the frame extending transverse to the direction of flow of the stream and including an opening through which the fluid material is passed between the near end and the far end of the frame as the stream of fluid material flows along the path of flow;

capturing means on the frame for capturing a volume of the fluid material of the stream to close off the captured volume of fluid material from the fluid material in the stream and for essentially confining the captured volume of fluid material against movement within the capturing means between the near end and the far end of the frame;

orifice means including an orifice member and drive means for advancing the orifice member into the volume of fluid material confined in the capturing means, the orifice member including an orifice through which the fluid material flows relative to the orifice as the orifice member is advanced through the confined captured volume of fluid material; and transducer means mounted on the frame for providing information pertaining to pressure in the confined volume of fluid material as the orifice member is advanced through the confined volume of fluid material, the pressure information being indicative of the rheological properties to be measured.

2. The rheometer of claim 1 wherein the orifice has essentially zero length in the direction of movement of the orifice member through the confined volume of fluid material.

3. The rheometer of claim 1 wherein the transducer means includes a transducer mounted on the frame adjacent the far end of the frame and the orifice means advances the orifice member in the direction from the near end toward the far end of the frame.

4. The rheometer of claim 1 wherein the transducer means includes a transducer mounted on the frame so as to remain stationary relative to the frame member as the orifice means advances the orifice member in the direction from the near end toward the far end of the frame.

5. The rheometer of claim 1 wherein the capturing means includes a tubular member movable along the frame in directions toward and away from the far end of the frame, and further drive means for advancing the tubular member toward the far end to capture the volume of fluid material and confine the captured volume of fluid material within the tubular member.

6. The rheometer of claim 5 wherein the orifice means includes a cylindrical member complementary to the tubular member for movement within the tubular member, the orifice member being carried by the cylindrical member so as to be urged against the captured volume of fluid material in the tubular member as the cylindrical member is moved in the direction toward the far end of the frame.

7. The rheometer of claim 6 wherein the orifice member is an orifice plate carried by the cylindrical member for movement with the cylindrical member, and the orifice has essentially zero length in the direction of movement of the orifice plate through the confined volume of fluid material.

* * * * *